United States Patent
Anderson et al.

(10) Patent No.: US 6,997,935 B2
(45) Date of Patent: Feb. 14, 2006

(54) RESONANT CONVERTER TUNING FOR MAINTAINING SUBSTANTIALLY CONSTANT PHACO HANDPIECE POWER UNDER INCREASED LOAD

(75) Inventors: David L. Anderson, Longmont, CO (US); Nate G. Elsen, Thornton, CO (US); Michael W. Fellinger, Boulder, CO (US); Pravin V. Mehta, Huntington Beach, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 583 days.

(21) Appl. No.: 09/989,795

(22) Filed: Nov. 20, 2001

(65) Prior Publication Data

US 2003/0097083 A1    May 22, 2003

(51) Int. Cl.
*A61B 17/32* (2006.01)
*G05F 1/00* (2006.01)
(52) U.S. Cl. .................. 606/169; 323/212; 323/215; 323/219
(58) Field of Classification Search ............. 606/169; 604/22; 601/2, 4; 702/124, 107; 310/316.01; 323/212, 215, 219
See application file for complete search history.

(56) References Cited

U.S. PATENT DOCUMENTS

| | | | |
|---|---|---|---|
| 3,990,452 A | 11/1976 | Murry et al. | |
| 4,849,872 A | 7/1989 | Gässler | |
| 5,001,649 A | 3/1991 | Lo et al. | 364/484 |
| 5,062,827 A | 11/1991 | Wiksell | |
| 5,331,951 A | 7/1994 | Kepley | 601/4 |
| 5,370,602 A | 12/1994 | Kepley | 601/2 |
| 5,406,503 A | 4/1995 | Williams, Jr. et al. | 364/571 |
| 5,852,794 A | 12/1998 | Staggs | 703/72 |
| 6,203,516 B1 | 3/2001 | Kepley | |
| 6,394,974 B1 * | 5/2002 | Kadziauskas et al. | 604/30 |
| 2001/0003155 A1 | 6/2001 | Rockley et al. | |

* cited by examiner

*Primary Examiner*—Tan-Uyen T. Ho
(74) *Attorney, Agent, or Firm*—Advanced Medical Optics, Inc.

(57) ABSTRACT

A phacoemulsification system includes a phacoemulsification handpiece including a cutting tip ultrasonically vibrated by an ultrasonic transducer. A power supply is provided for driving the ultrasonic transducer at a resonant frequency of the transducer and cutting tip and varying power to the transducer, in response to loading of the cutting tip, by phase shifting drive signals to the resonant converter which supplies power to the transducer.

19 Claims, 5 Drawing Sheets

RESONANT CONVERTER TUNING FOR MAINTAINING SUBSTANTIALLY CONSTANT PHACO HANDPIECE POWER UNDER INCREASED LOAD

The present invention generally relates to circuits and methods for driving ultrasonic transducers and more particularly is directed to controlling ultrasonic transducers in phacoemulsification handpieces used for ophthalmic surgical procedures.

Phacoemulsification is known as a process for disintegration of the lens of an eye utilizing a probe vibrating at ultrasonic frequencies. Typically such handpieces include a piezoelectric crystal transducer operatively connected to a needle, having a cutting tip, which is vibrated at ultrasonic frequencies to shatter, or disintegrate cataractic tissue. Fragmented lens tissue is aspirated through a lumen and the handpiece typically provides for introducing irrigation fluid into the eye to both assist in the aspiration of the disintegrated lens and to maintain proper pressure in the eye.

The needle is supported by a phacoemulsification handpiece which also houses piezoelectric crystals and a horn vibrating the needle. Structural details of such phacoemulsification handpieces are well known in the art.

During phacoemulsification, the cutting tip is inserted through a small incision in the cornea, sclera, or other location to provide access to the anterior chamber of the eye. Thereafter the cutting tip is ultrasonically vibrated by the piezoelectric crystal which causes disintegration and/or emulsification of tissue in contact with the cutting tip.

The piezoelectric crystals convert the electrical energy into mechanical energy to cause vibration in the horn and needle. It has been found that piezoelectric crystals operate at specific frequencies more efficiently than at other frequencies. These specific frequencies are known as "resonant" frequencies. Thus, it is well known that the frequency of applied electrical power to the handpiece should be adjusted, or tuned, to the resonant frequency for efficient power conversion.

Heretofore, ultrasonic phacoemulsification handpieces utilizing piezoelectric ceramic drive elements have been driven, or powered, by linear power amplifiers, switching power amplifiers, or a combination of the two. A typical linear drive is set forth in U.S. Pat. No. 5,331,951 which describes a drive for phacoemulsification handpiece which includes a drive circuit for supplying electrical power to the handpiece, circuitry for sensing the electrical power supplied by the drive circuit to the handpiece and for supplying electrical hand signals indicative of the magnitude of the electrical power supplied.

A control circuit is responsive to the signal indicative of the desired transducer power level and to the signals indicative of the magnitude of the supplied electrical power for providing control signals to the drive circuit to control the power applied.

The advantages of linear power amplifiers are flat amplitude response with variation in handpiece resonant frequency, good load regulation and low EMI-RFI. However, such linear amplifiers have poor electrical efficiency resulting in increased power and cooling requirements.

Switching power amplifiers are desirable for greater electrical efficiency, however the disadvantages associated with switching power amplifiers are higher operating frequency, output filter requirements, and amplitude response irregularities. A switching driver made operate to vary the pulse width of the wave form provided to the handpiece in order to vary the amount of electrical power supplied to the transducer is described in U.S. Pat. No. 5,370,602.

A phase shift resonant power converter has been developed which maintains reasonable amplitude response and load regulation which is hereinafter described.

SUMMARY OF THE INVENTION

A phacoemulsification system in accordance with the present invention generally includes a phacoemulsification handpiece with a tip ultrasonically vibrated by an ultrasonic transducer. A power supply is provided for driving the ultrasonic transducer and cutting tip at a resonant frequency. Driving power to the transducer is varied in response to loading of the cutting tip, by controlling the phase shift between the voltage and current applied to the transducer.

More particularly, the power supply includes a resonant output circuit, connected to the ultrasonic transducer, having an output voltage and an output current oscillating therethrough. A current sensor provides a current signal corresponding to the output current and a voltage sensor provides a voltage signal corresponding to the output voltage. A bridge driver is provided for controlling the resonant output circuit with the bridge driver being responsive to driver signals.

Control circuitry provides an amplitude command in response to the current and voltage signals and a frequency command corresponding to the operating frequency.

Phase shift circuitry responsive to the frequency and amplitude commands is provided for producing the driver signals in order to control the power output of the resonant output circuit through the bridge driver by phase shifting the output voltage of one side of the bridge relative to the other. The resonant circuit provides simple and effective filtering of the output. The bridge driver operates at the actual handpiece frequency which is relatively low, for example between about 20 KHz to about 60 KHz. This results in reduced transistor switching losses and transformer losses. As will be hereinafter discussed in greater detail, the circuitry of the present invention is tolerant of transformer leakage inductance and 0 voltage switching can be achieved which also reduces losses. In addition, reduced EMI and RFI result since the voltage and current switching wave forms are much "cleaner" with slower edges then converters using Pulsed Width Modulation as hereinabove noted.

According to the present invention, the bridge driver may comprise a full bridge converter which provides a square wave to the resonant output circuit. The resonant output circuit includes a step-up transformer with a primary winding connected to the bridge driver and a secondary winding connecting to an inductor parallel resonant circuit in order that any transformer leakage adds to the total inductance.

More particularly, the phase shift circuitry produces a copy of the frequency command which is shifted in phase based upon the amplitude command and inverted to produce 4 driver signals. The frequency command is shifted between 0 and 180° based upon the amplitide command of 0 to 100%.

BRIEF DESCRIPTION OF THE DRAWINGS

The advantages and features of the present invention will be better understood by the following detailed description considered in connection with the accompanying drawings, in which.

DETAILED DESCRIPTION

Figure 1:
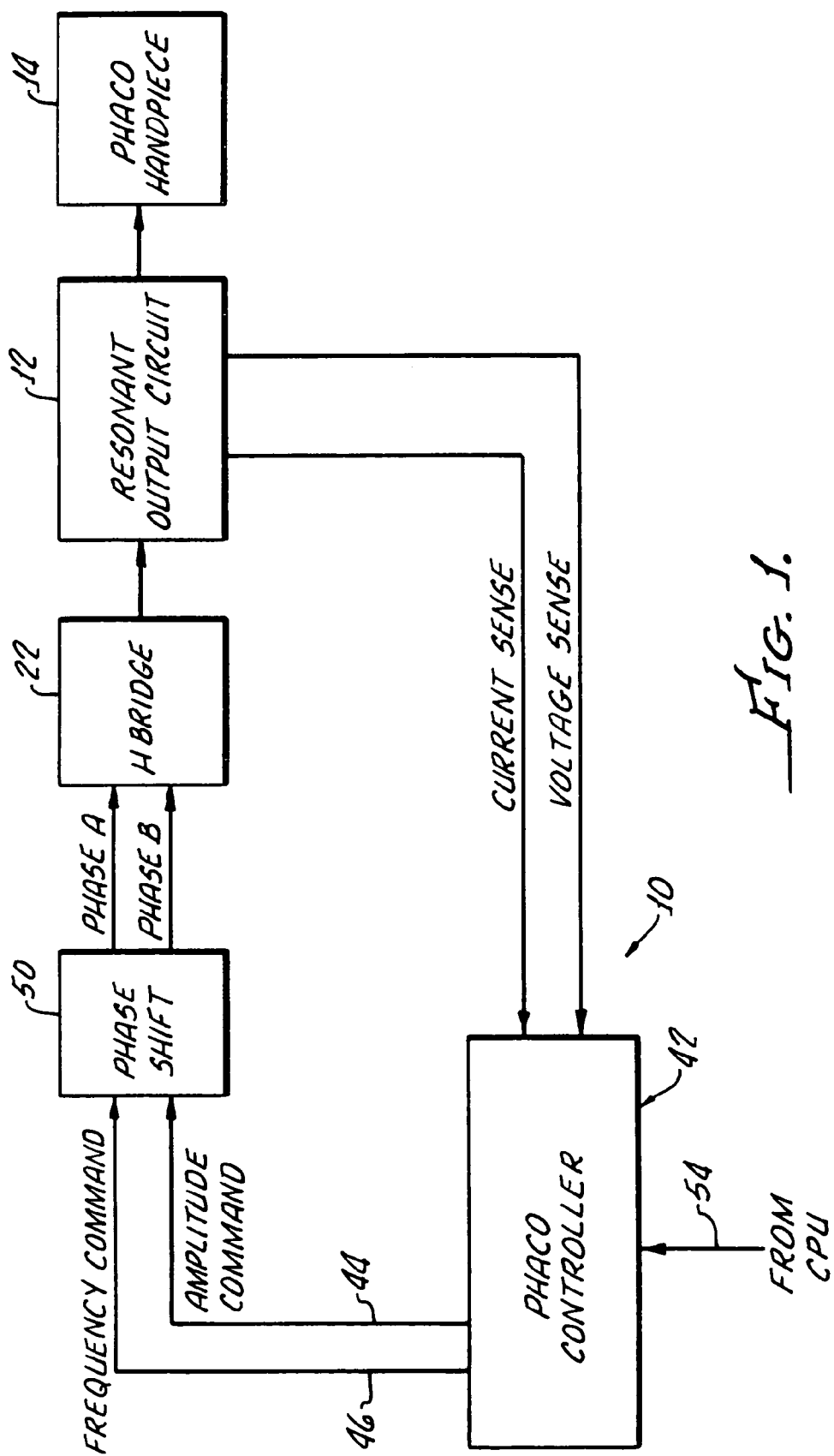
FIG. 1 is a block diagram of the present invention; showing phase shift circuitry, a bridge driver, resonant output circuitry connected to a phaco handpiece and a phaco controller.
Figure 2:
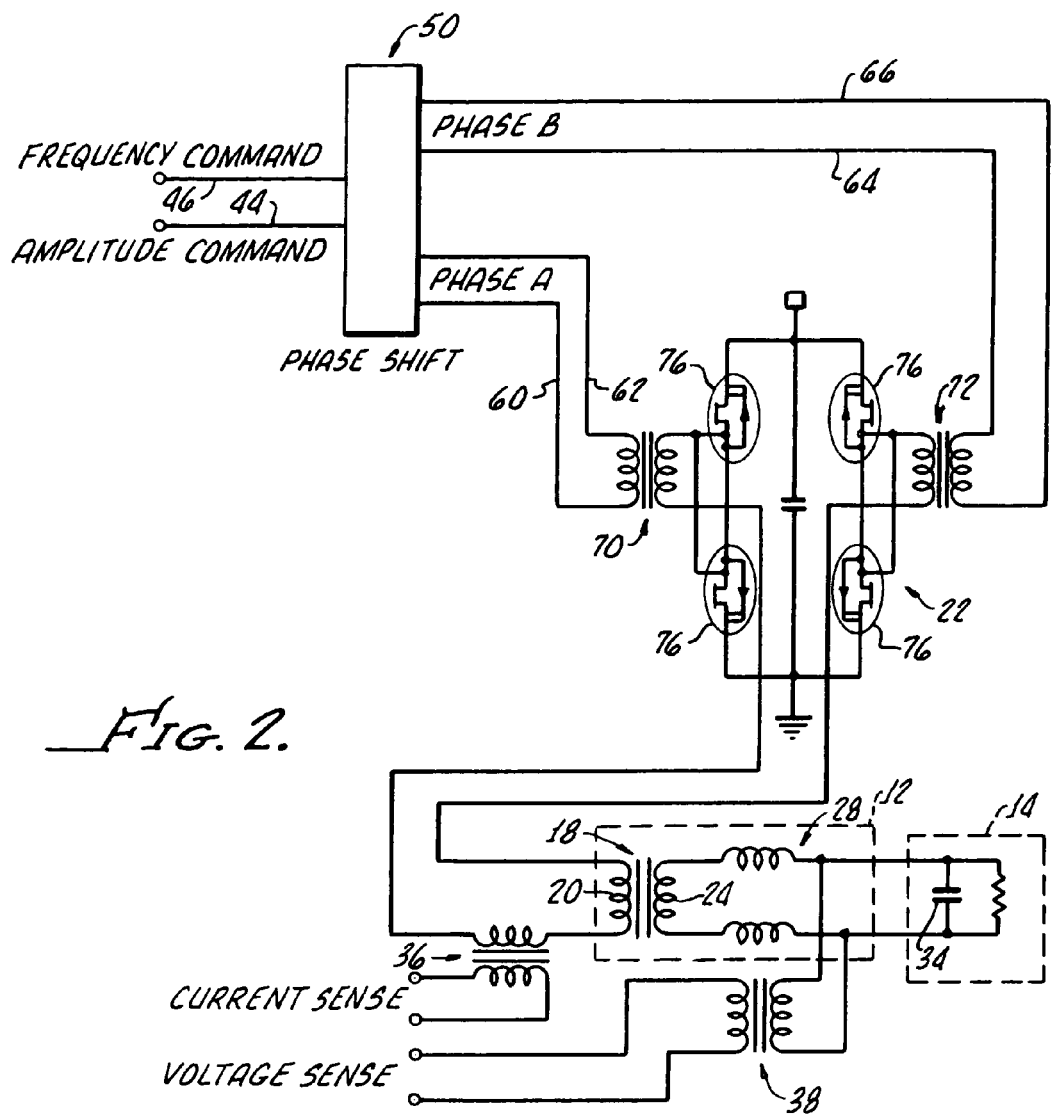
FIG. 2 is a schematic showing in greater detail the phase shift circuitry, the bridge driver and resonant output circuitry along with current and voltage sensors.
Figure 3A:
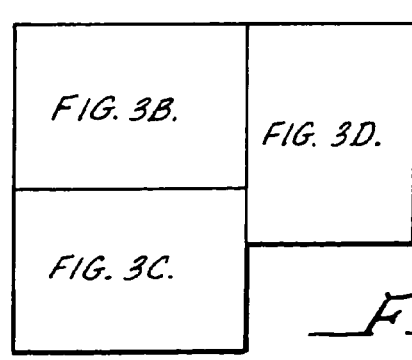
FIG. 3 is an overall circuit schematic of the present invention.
Figure 3B:
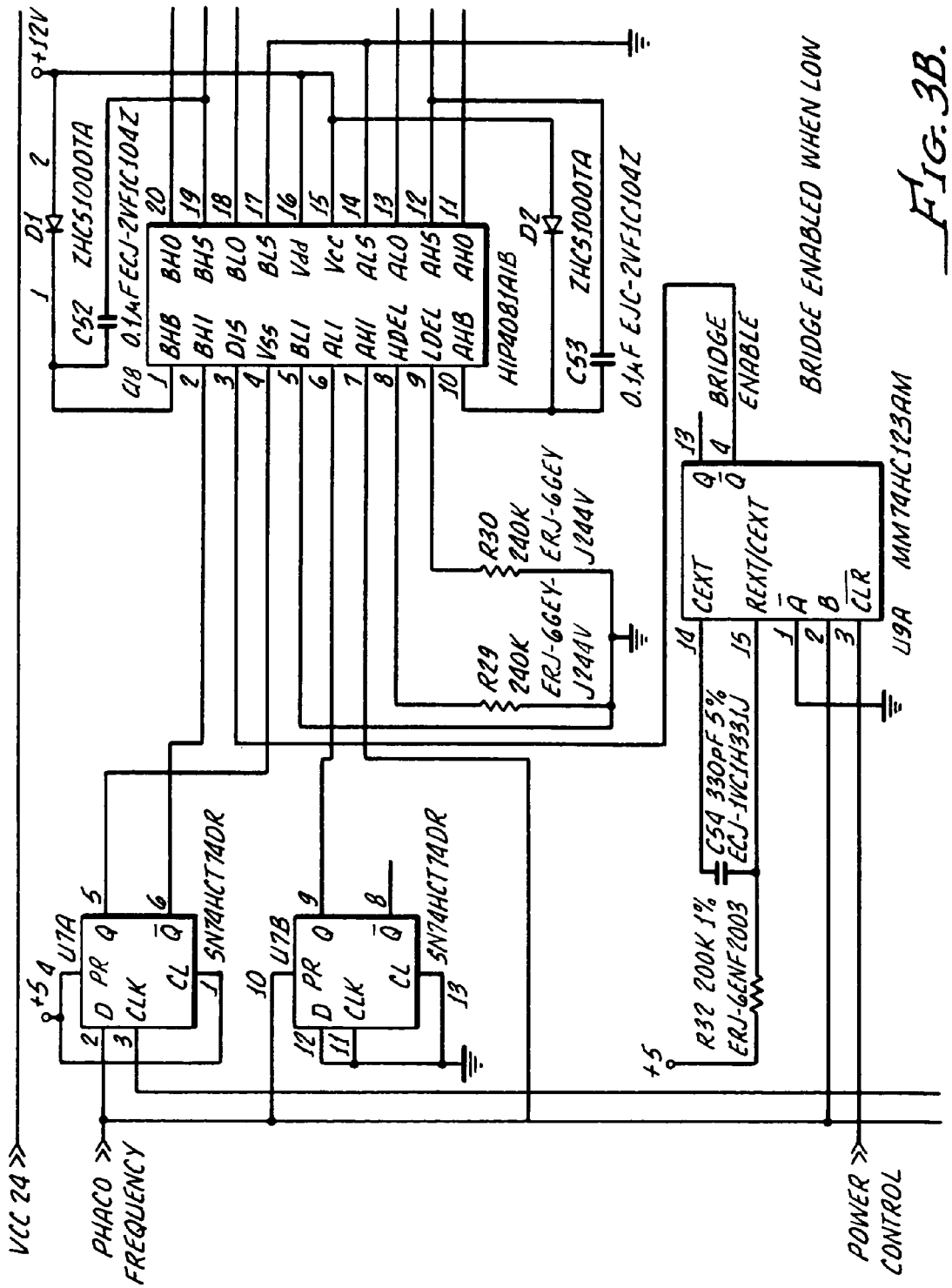
Figure 3C:
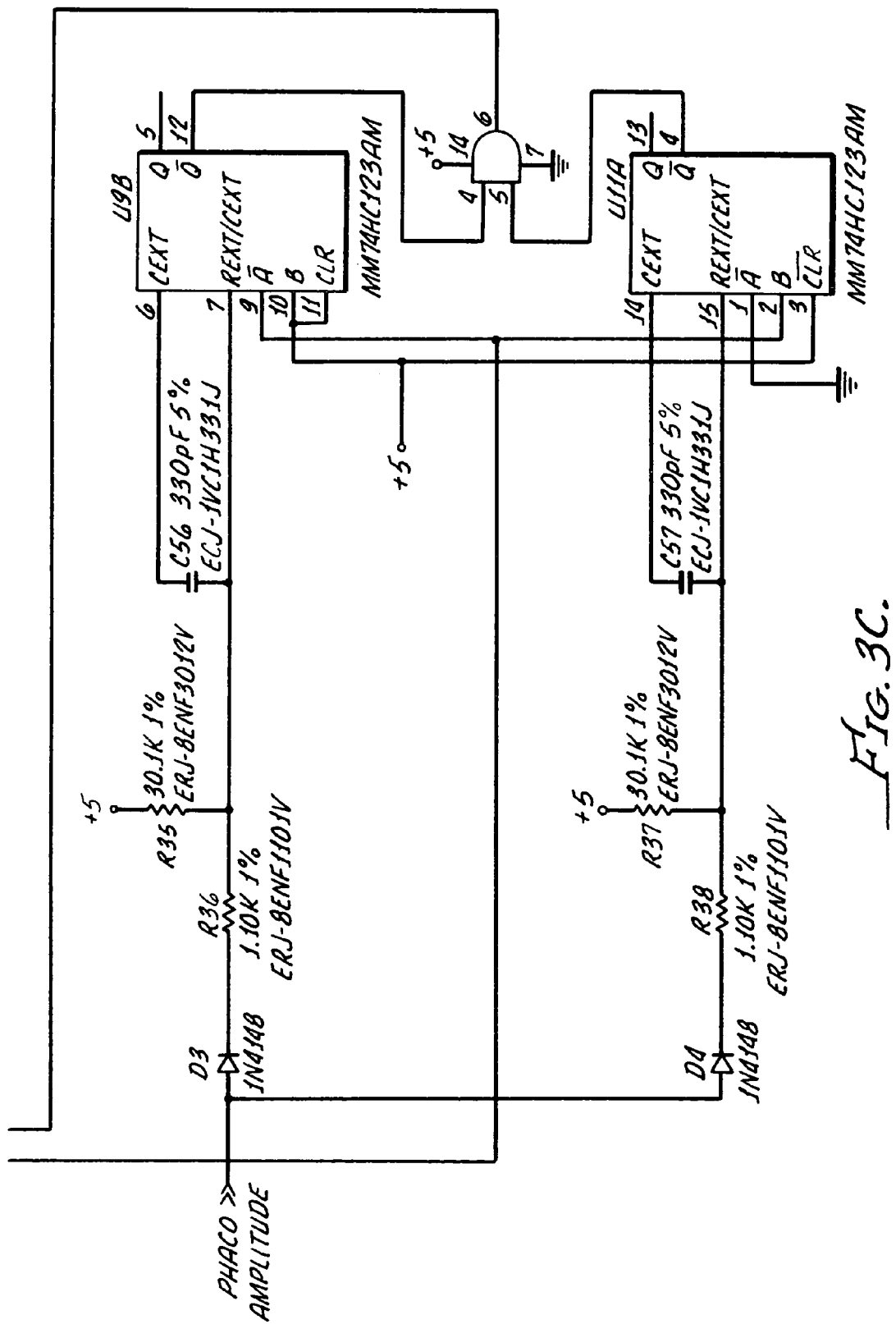
Figure 3D:
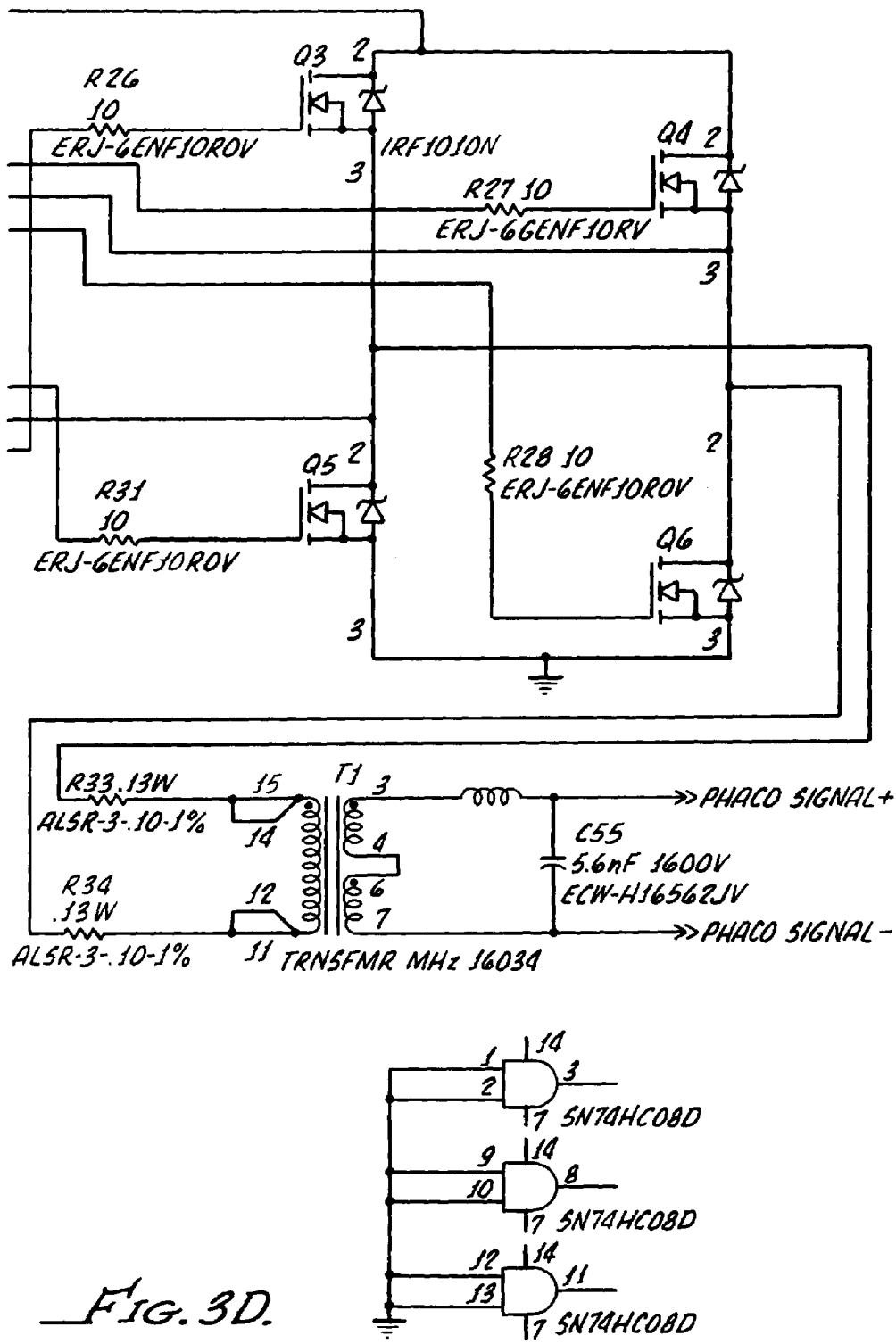

With reference to FIGS. 1–3, a phacoemulsification system 10 in accordance with the present invention generally includes a resonant output circuit 12 connected to an ultrasonic transducer within and represented by a phaco handpiece 14. The resonant output circuit includes a step-up transformer 18 having a primary winding 20 interconnected with a bridge driver 22 and a secondary winding 24 connected in series with an inductive parallel resonant circuit 28 such that any leakage inductance adds to the total inductance.

A capacitor 34 is provided to tune the resonant frequency to the desired point when shunted by the handpiece 14 impedance. Typically the resonant frequency will be selected to be near, or at, the handpiece 14 resonance. Thus, the resonant circuit 12 is tuned to enhance the open loop load response, i.e., output voltage increase with load impedance increase.

A current sensor 36 provides a current signal corresponding to the output current and a voltage sensor 38 provides a voltage signal corresponding to the output voltage of the resonant circuit 12. These signals are provided to a phaco controller 42 which produces an amplitude command indicated by the arrow 44 in response to the current voltage signals and a frequency command 46 which provides input to phase shift circuitry 50 in response to input indicated by the arrow 54 from a phaco console CPU (not shown).

The drive frequency/phase can be controlled to maintain or increase the power factor. Active control can also independently or concurrently increase the amplitude of the voltage delivered to the handpiece to maintain power. If constant phase is elected in conjunction with a constant voltage, the power will decrease with loading of the handpiece 14.

Passive control through the resonant output circuit 12 is also possible. The resonant tank circuitry 12 can be tuned with a center frequency near that of the desired handpiece operating frequency, thus, as the handpiece 14 impedance increases the Q of the resonant tank circuit 12 increases which results in more voltage output to the handpiece 14. This results in maintaining relatively constant handpiece power.

The phase shift circuitry 20 may include circuitry composed of analog and digital componentry arranged to produce a time delay corresponding to an analog or digital command signal. This circuit produces a copy of the frequency input, or command, 46 which is shifted to phase (approximately 0 to 180°) based upon the amplitude input command 44 (0 to 100% power) from the phaco controller 42. The frequency input, and the phase shifted version are then each inverted. The resulting four signals, represented by lines 60, 62, 64, 66 are fed to the inputs 70, 72 of the bridge driver 22. The bridge driver 22 is preferably a full bridge inverter which produces a square wave to the resonant output circuit 12 and may be a commercially available H-bridge driver (Intersil HIP 4081 A). The H-bridge driver 22 drives four N-channel Power MOSFETS (IRF 1010N) 76 which make up the H-bridge 22.

Although there has been hereinabove described a phacoemulsification system in accordance with the present invention for the purpose of illustrating the manner in which the invention may be used to advantage, it should be appreciated that the invention is not limited thereto. Accordingly, any and all modifications, variations, or equivalent arrangements which may occur in those skilled in the art, should be considered to be within the scope of the present invention as defined in the appended claims.

What is claimed is:

1. A phacoemulsification system comprising:
   a phacoemulsification handpiece including a cutting tip ultrasonically vibrated by an ultrasonic transducer;
   a power supply for driving said ultrasonic transducer at a resonant frequency of the transducer and cutting tip and varying driving power to the transducer, in response to loading of said cutting tip, by phase shifting voltage and current supplied to the transducer.

2. The system according to claim 1 wherein said power supply comprises:
   a resonant output circuit connected to the ultrasonic transducer and having an output voltage and an output current oscillating therethrough;
   a current sensor for providing a current signal corresponding to said output current;
   a voltage sensor for providing a voltage signal corresponding to said output voltage;
   a bridge driver for controlling said resonant output circuit, said bridge driver being responsive to driver signals;
   control circuitry for producing an amplitude command in response to the current and voltage signals and a frequency command; and
   phase shift circuitry responsive to the frequency and amplitude commands for producing the driver signals, in order to control power output of said resonant output circuit through said bridge driver, by phase shifting the output voltage of one side of the bridge driver with respect to another side of the bridge circuit.

3. The system according to claim 2 wherein said bridge driver provides a square wave to said resonant output circuit.

4. The system according to claim 3 wherein said bridge driver comprises a full-bridge invertor.

5. The system according to claim 4 where said resonant output current includes a step-up transformer.

6. The system according to claim 5 wherein said step-up transformer includes a primary winding connection to said bridge driver.

7. The system according to claim 6 where said step-up transformer includes a secondary winding connected to an inductor of a parallel resonant circuit in order that any transformer leakage adds to the total inductance.

8. The system according to claim 7 wherein said phase shift circuitry produces a copy of the frequency command which is shifted in phase based on the amplitude commands and inverted to produce four driver signals.

9. The system according to claim 8 wherein said copy of the frequency command is shifted between 0 and 180 degrees based on the amplitude command of 0 to 100 percent from said control circuitry.

10. A phacoemulsification system comprising:
    a phacoemulsification handpiece including cutting tip ultrasonically vibrated by an ultrasonic transducer;
    a resonant output circuit connected to the ultrasonic transducer and having an output voltage and an output current oscillating therethrough;
    a current sensor for providing a current signal corresponding to said output current;
    a voltage sensor for providing voltage signal corresponding to said output voltage;

a bridge driver for controlling said resonant output circuit, said bridge driver being responsive to driver signals;

control circuitry for producing an amplitude command in response to the current and voltage signals and a frequency command; and phase shift circuitry responsive to the frequency and amplitude commands for producing the driver signals, in order to control power output of said resonant output circuit through said bridge driver, by phase shifting the output voltage and output current.

11. The system according to claim 10 wherein said resonant output circuit is configured for oscillating at a resonant frequency of the ultrasonic transducer and cutting tip.

12. The system according to claim 11 wherein said bridge driver provides a square wave to said resonant output circuit.

13. The system according to claim 12 wherein said bridge driver comprises a full bridge inverter.

14. The system according to claim 13 wherein said resonant output circuit includes a step-up transformer.

15. The system according to claim 14 wherein said step-up transformer includes a primary winding connected to said bridge driver.

16. The system according to claim 15 wherein said step-up transformer includes a secondary winding connection to an inductor of a parallel resonant circuit in order that any transformer leakage adds to the total inductance.

17. The system according to claim 16 wherein said phase shift circuitry providing a copy of the frequency command which is shifted in phase based on the amplitude command and inverted to produce four driver signals.

18. The system according to claim 17 wherein said copy of the frequency command is shifted between 0 and 180 degrees based on the amplitude command of 0 to 100 percent from said control circuitry.

19. The system according to claim 10 wherein said resonant output circuit is tuned to enhance open loop load response of the transducer.

* * * * *